United States Patent [19]

Priou

[11] Patent Number: 5,693,688

[45] Date of Patent: Dec. 2, 1997

[54] INITIATORS FOR THE CATIONIC CROSSLINKING OF POLYMERS CONTAINING ORGANOFUNCTIONAL GROUPS, CROSSLINKABLE POLYORGANOSILOXANE-BASED COMPOSITIONS CONTAINING THESE INITIATORS AND APPLICATION OF SAID COMPOSITIONS IN ANTI-ADHESION

[75] Inventor: Christian Priou, Villeurbanne, France

[73] Assignee: Rhone-Poulenc Chimie, Courbevoie Cedex, France

[21] Appl. No.: 528,926

[22] Filed: Sep. 15, 1995

[30] Foreign Application Priority Data

Sep. 16, 1994 [FR] France ................... 94 11463

[51] Int. Cl.$^6$ ................................................. C08F 2/46
[52] U.S. Cl. ................................. 522/25; 522/29; 522/99
[58] Field of Search ....................... 522/25, 29, 99

[56] References Cited

U.S. PATENT DOCUMENTS

| | | | |
|---|---|---|---|
| 4,694,029 | 9/1987 | Land | 522/8 |
| 5,340,898 | 8/1994 | Cavezzan et al. | 522/64 |

FOREIGN PATENT DOCUMENTS

| | | |
|---|---|---|
| 0 522 703 A2 | 1/1993 | European Pat. Off. . |
| 0 562 897 A1 | 9/1993 | European Pat. Off. . |
| 0 562 922 A1 | 9/1993 | European Pat. Off. . |
| 0 614 958 A1 | 9/1994 | European Pat. Off. . |

*Primary Examiner*—Mark Chapman
*Attorney, Agent, or Firm*—Burns, Doane, Swecker & Mathis, L.L.P.

[57] ABSTRACT

The present invention relates to initiators of cationic polymerization and/or crosslinking, under photochemical and/or thermal activation and/or activation by a beam of electrons, of monomers and/or polymers containing organofunctional groups.

These initiators give good performance with the majority of monomers/polymers, including in particular functional polyorganosiloxanes, which are crosslinkable cationically and under UV.

The subject of the invention is also compositions based on at least one cationically crosslinkable polyorganosiloxane and on at least one initiator, as defined above.

Application: paper anti-adhesion.

13 Claims, 1 Drawing Sheet

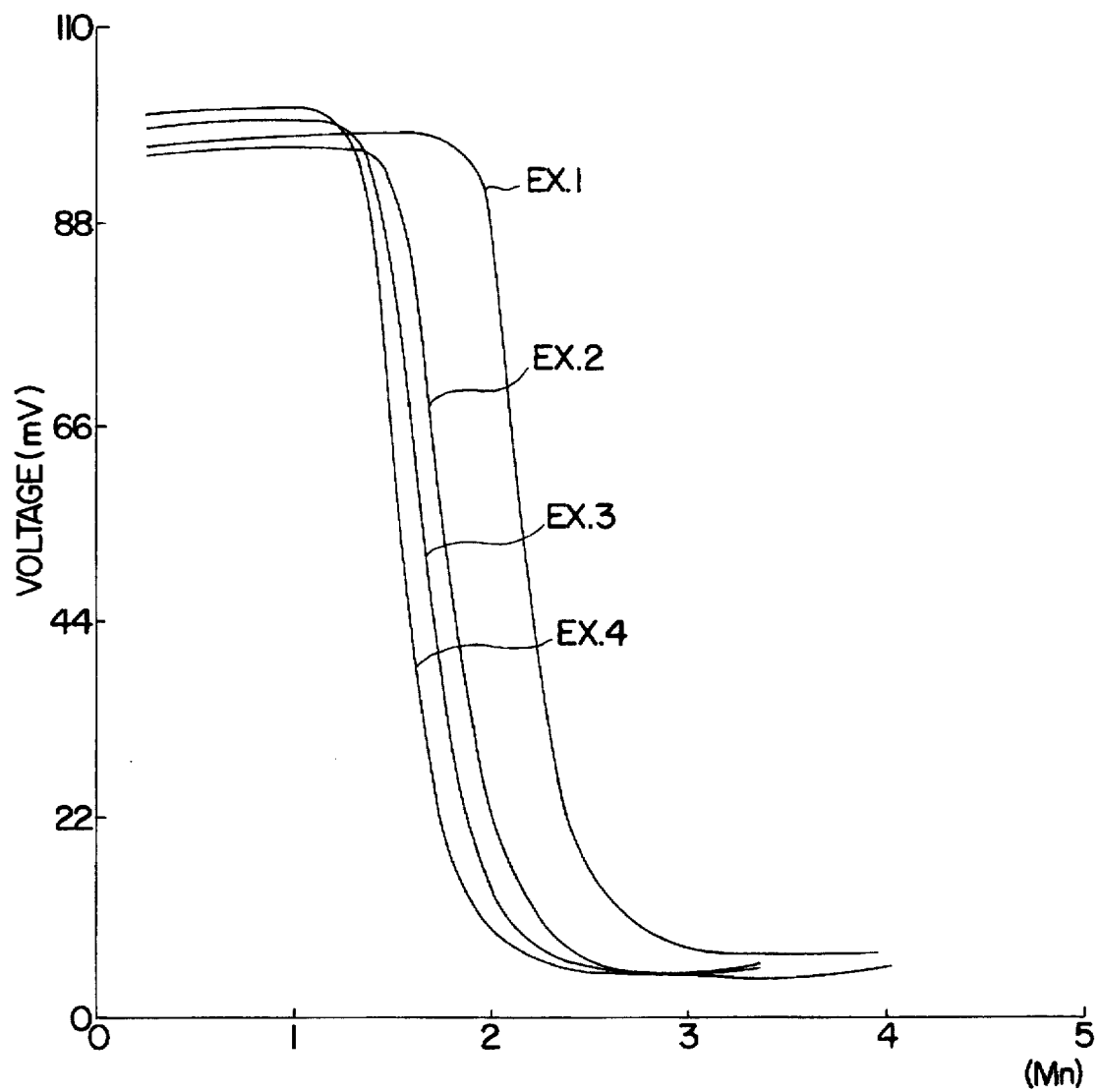

INITIATORS FOR THE CATIONIC CROSSLINKING OF POLYMERS CONTAINING ORGANOFUNCTIONAL GROUPS, CROSSLINKABLE POLYORGANOSILOXANE-BASED COMPOSITIONS CONTAINING THESE INITIATORS AND APPLICATION OF SAID COMPOSITIONS IN ANTI-ADHESION

The field of the invention is that of the catalysis of cationic polymerization and/or crosslinking reactions of monomers and/or polymers, e.g. those containing silicon, comprising reactive functional radicals capable of forming intra- and inter-chain bridges, so as to obtain a polymerized and/or crosslinked material having a certain hardness and a certain mechanical strength.

More precisely, the subject of the present invention is initiators of cationic polymerization and/or crosslinking. Although these initiators are not catalysts in the strict sense, they may nevertheless be likened to catalytic compounds which allow the initiation and progress of the reaction for the formation of polymers and/or crosslinked materials, starting with substrates formed of monomers and/or polymers containing reactive organofunctional groups.

The reactions more particularly concerned are those in which cationic agents act as direct promoters of the inter- and/or intra-chain bonding.

Traditionally, these reactions can only take place under photochemical and/or thermal activation and/or activation by a beam of electrons. In practice, it is, for example, the light energy of a UV radiation beam which allows the formation of the active protagonists, for example by radical cleavage, and hence the triggering and continuation of the crosslinking and/or polymerization.

Without this being limiting, it is more particularly a question, in the present account, of polymerized or crosslinked substrates of polyorganosiloxane type containing reactive organofunctional groups, for example of the epoxide and/or vinyl ether type. These functional polyorganosiloxanes which are crosslinkable via a cationic route and using the initiators intended above, may be used in particular for the production of anti-adhesive coatings on solid articles or supports (e.g. paper, polymer film of the polyester, polyethylene, etc. type).

The subject of the invention is thus also compositions based on crosslinkable functional polyorganosiloxanes and the above-intended initiators.

The invention also relates to the application of these compositions as coatings for solid articles or supports, these coatings themselves also constituting a subject of the invention.

Cationic initiators of polymerization or crosslinking, e.g. via the photochemical route, of functional monomers or polymers of the polyorganosiloxane type in particular, are described in European patent application No. 0,562,897 in the name of the Applicant. These photo-initiators consist of onium borates of an element from groups 15 to 17 of the Periodic Table (Chem. & Eng. News, Vol. 63, N5, 26 of 4 Feb. 1985) or of an organometallic complex of an element from groups 4 to 10 of the Periodic Table (Chem. & Eng. News, Vol. 63, N5, 26 of 4 Feb. 1985), in which the anionic borate species has the formula:

[BX<sub>a</sub>R<sub>b</sub>]<sup>−</sup>

in which formula:
a and b are integers ranging from 0 to 4 with a+b=4,
the symbols X represent:

a halogen atom (chlorine, fluorine) with a=0 to 3,
an OH function with a=0 to 2,
the symbols R are identical or different and represent:
  a phenyl radical substituted with at least one electron-withdrawing group or with at least two halogen atoms,
  an aryl radical containing at least two aromatic rings optionally substituted with at least one element or one electron-withdrawing group.

These novel self-initiating salts represent an appreciable technical advance when compared with the known initiators of onium salt type or of organometallic complex type, and in particular when compared with those in which the anion of the initiator salt is $SbF_6^-$ which is one of the only ones which gives good catalytic performance, but which poses serious problems of use on account of its toxicity.

The photo-initiator salts according to EP-A-0,562,897 are employed in combination with an alcohol, such as methanol, in order to produce anti-adhesive coatings on paper, starting with epoxidized monomers, which are crosslinked by UV irradiation. In order to assess the performance of the photo-initiator, the reactivity of the substrate/initiator pair and the rate of crosslinking are evaluated by means of the rate of throughput required for curing of the layer applied to the paper, as well as by means of the number of passages.

The polyorganosiloxane-based compositions which are crosslinkable using onium borates according to EP-A-0,562,897, are described and claimed in European patent application No. 0,562,922, also in the name of the Applicant. According to the latter document, the photo-initiator systems used include the onium borate and an alcoholic solvent of the methanol or 2-ethylhexanediol type. The quality of the coatings obtained reflects the performance of these photo-initiator systems. In order to assess this quality of coating, the anti-adhesive properties of the layer of crosslinked silicone polymer bound to the support are evaluated. The results measured are acceptable, but it nevertheless remains that in order to satisfy the productivity requirements of those applying these coatings, the initiator systems need to give increasingly good performance. They must thus make it possible to achieve crosslinking/polymerization rates and reactivities which are as high as possible, so as to be able to increase the rates of coating.

Given this situation, one of the essential aims of the present invention is to satisfy the abovementioned requirements.

Another essential aim of the invention is to provide initiators which perform well with the majority of monomers/polymers, in particular including functional polyorganosiloxanes, which are crosslinkable cationically and under UV.

Another essential aim of the invention is to provide effective but also inexpensive cationic initiators which are easy to handle and have little toxicity.

Another aim of the invention is to provide organofunctional monomer/polymer compositions, in particular organofunctional polyorganosiloxanes, which are crosslinkable cationically and under light and/or heat and/or electron-beam activation.

Another aim of the invention is to provide a process for the coating of solid articles or supports using the above-said compositions, as well as the resulting articles obtained with a crosslinked, anti-adhesive coating.

These aims and others are achieved by the invention, which relates, firstly, to initiators for the cationic polymerization and/or crosslinking, under photochemical and/or thermal activation and/or activation by a beam of electrons, of monomers and/or polymers containing organofunctional groups, said initiators comprising an effective catalytic amount of at least one onium salt of an element from groups 15 to 17 of the Periodic Table (Chem. & Eng. News, Vol. 63, N5, 26 of 4 Feb. 1985) and/or of at least one organometallic complex of an element from groups 4 to 10 of the Periodic Table (Chem. & Eng. News, Vol. 63, N5, 26 of 4 Feb. 1985), characterized in that they contain at least one polymerization and/or crosslinking accelerator chosen from proton-donating organic solvents of aromatic nature.

These accelerators make it possible to improve significantly the performance of the cationic initiators in terms of reactivity and kinetics. The Applicant has, to its credit, been able to isolate a family of special organic solvents which is particularly suitable for use as accelerator.

The accelerator is preferably formed of at least one benzyl alcohol of the following general formula

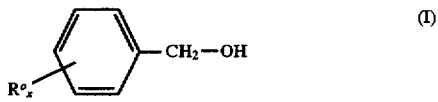

in which:
R° is an electron-donating or electron-accepting group, preferably an electron-accepting group, chosen from linear or branched $C_1$–$C_{12}$ (cyclo)alkyls and (cyclo)alkoxyls, aryls, which are optionally substituted preferably with halogens, or radicals of the type $NO_2$ etc.,
x is an integer from 0 to 5,
and the groups R° being identical to or different from each other when x>1,
the formulae (I) in which x=0 or those in which x>0 with R° representing a methyl, t-butyl or isopropyl group, being particularly preferred.

This preferred sub-family of accelerators of benzyl alcohol type contains compounds which perfectly fulfill the main function intended but which have, in addition, the advantage of being very economic, having little toxicity, and being easy to handle and compatible with the known cationic initiator salts.

In practice, the proportions by weight between the initiator salt or salts, in particular the onium borates, on the one hand, and the accelerator, on the other hand, expressed in parts by weight, are respectively between 0.1:100 and 1:0.5, preferably between 2:100 and 1:1, this last proportion being particularly preferred.

In accordance with an advantageous provision of the invention, the initiators comprise an effective catalytic amount of an onium borate
* the cationic species of which is chosen from:
  1) the onium salts of formula (II)

$$[(R^1)_n\text{—}A\text{—}(R^2)_m]^+ \quad (II)$$

in which formula:
A represents an element from groups 15 to 17, such as I, S, Se, P, N, etc.,
$R^1$ represents a $C_6$–$C_{20}$ carbocyclic or heterocyclic aryl radical, preferably phenyl, tolyl or toluyl, it being possible for said heterocyclic radical to contain nitrogen or sulfur as hetero elements, etc.,
$R^2$ represents $R^1$ or a $C_1$–$C_{30}$ linear or branched alkyl or alkenyl radical, said radicals $R^1$ and $R^2$ being optionally substituted with a $C_1$–$C_{25}$ alkoxy, $C_1$–$C_{25}$ alkyl, nitro, chloro, bromo, cyano, carboxyl, mercapto, etc. group,
n is an integer ranging from 1 to v+1, v being the valency of the element A, m is an integer ranging from 0 to v−1 with n+m=V+1, 2) the oxoisothiochromanium salts described in patent application WO-A-90/11303, in particular the sulfonium salt of 2-ethyl-4-oxoisothiochromanium or of 2-dodecyl-4-oxoisothiochromanium, 3) the organometallic salt of formula (II bis):

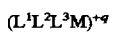

in which formula:

M is a metal from Groups 4 to 10 of the Periodic Table, especially iron, manganese, chromium, cobalt, and the like; $L^1$ is one ligand joined to the metal M via π electrons, said ligand being selected from among the $\eta^3$-alkyl, $\eta^5$-cyclopentadienyl and $\eta^7$-cycloheptatrienyl ligands and the $\eta^6$-aromatic compounds selected from among the optionally substituted $\eta^6$-benzene ligands and the compounds having from 2 to 4 condensed rings, each ring being capable of contributing to the valence shell of the metal M via 3 to 8 π electrons; $L^2$ is one ligand joined to the metal M via π electrons, said ligand being selected from among the $\eta^7$-cycloheptatrienyl ligands and the $\eta^6$-aromatic compounds selected from among the optionally substituted $\eta^6$-benzene ligands and the compounds having from 2 to 4 condensed rings, each ring being capable of contributing to the valence shell of the metal M via 6 or 7 π electrons; $L^3$ is from 0 to 3 identical or different ligands joined to the metal M via σ electrons, said ligand(s) being selected from among CO and $NO_2^+$, with the proviso that the total electron charge q of the complex to which $L^1$, $L^2$ and $L^3$ contribute and the ionic charge of the metal M are positive and equal to 1 or 2.

* the anionic borate species of which has the formula (III):

$$[BX_aR_b] \quad (III)$$

in which formula:

a and b are integers ranging from 0 to 4 with a+b=4, the symbols X represent:
  a halogen atom (chlorine or fluorine) with a=0 to 3,
  an OH function with a=0 to 2, the symbols R are identical or different and represent:
  a phenyl radical substituted with at least one electron-attracting group such as $CF_3$, $NO_2$, CN, etc., or with at least two halogen atoms (most particularly fluorine),
  an aryl radical containing at least two aromatic rings, such as biphenyl, naphthyl, etc., which is optionally substituted with at least one electron-attracting element or group, in particular a halogen atom (most particularly fluorine), $CF_3$, $NO_2$, CN, etc.

The anionic borate species is advantageously chosen from the following anions:

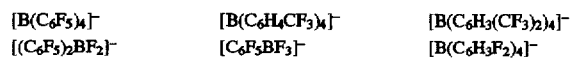

As regards the cationic species, which is advantageously of onium type, this is more preferably selected from the following cations:

[(Φ)₂I]⁺    [C₈H₁₇—O-Φ-I-Φ]⁺    [(Φ-CH₃)₂I]⁺
[C₁₂H₂₅-Φ-I-Φ]⁺    [(C₈H₁₇—O-Φ)₂I]⁺
[(Φ)₃S]⁺    [(Φ)₂-S-Φ-O—C₈H₁₇]⁺
[Φ-S-Φ-S-(Φ)₂]⁺    [(C₁₂H₂₅-Φ)₂I]⁺

In accordance with the invention, the initiators which will more preferably be used are the following onium borates:

[(Φ-CH₃)₂I]⁺[B(C₆F₅)₄]⁻
[(Φ)₂I]⁺[B(C₆F₅)₄]⁻    [Φ₂I]⁺[B(C₆H₃(CF₃)₂)₄]⁻
[C₁₂H₂₅-Φ-I-Φ]⁺[B(C₆F₅)₄]⁻    [(C₈H₁₇—O-Φ)₂I]⁺[B(C₆F₅)₄]⁻
[(C₈H₁₇)—O-Φ-I-Φ]⁺[B(C₆F₅)₄]⁻    [(Φ)₃S]⁺[B(C₆F₅)₄]⁻
[(Φ)₂S-Φ-O—C₈H₁₇]⁺[B(C₆H₄CF₃)₄]⁻    [(C₁₂H₂₅-Φ)₂I]⁺[B(C₆F₅)₄]⁻

The onium borates or the borates of organometallic complexes, and more particularly the onium borates, entering into the formulation of the initiator system according to the invention are defined in detail in the abovementioned European patent applications Nos. 0,562,897 and 0,562,922. The content of these patent applications is incorporated into the present account by way of reference.

In practice, the initiators according to the invention are prepared in a very simple manner by dissolving the onium borate or the borate of the organometallic complex, preferably the onium borate, which is in solid (powder) form, in the accelerator, which advantageously consists of a solvent of the benzyl alcohol type.

According to an alternative relating to the onium borate, the latter may be prepared directly in the accelerator, from a salt (e.g. chloride) of the cation (iodonium) and from a salt (for example the potassium salt) of the borate anion.

The precursor system thus obtained may be used in monomer/polymer compositions, one which is polymerized/crosslinked cationically and under activation, for example UV activation.

According to another of these aspects, the present invention relates to compositions based on at least one cationically crosslinkable polyorganosiloxane and on at least one initiator of the type such as those in accordance with the invention which have been described above.

This polyorganosiloxane preferably has organofunctional groups of the epoxide and/or vinyl ether type and it is chosen from polyorganosiloxanes which are:

either linear or substantially linear and consist of units of formula (IV), ending with units of formula (V), or cyclic and consist of units of formula (IV):

(IV)

(V)

in which formulae:

the symbols R³ are similar or different and represent:
either a linear or branched C₁-C₆ alkyl radical, which is optionally substituted, advantageously with one or more halogens, the optionally substituted alkyl radicals preferred being: methyl, ethyl, propyl, octyl and 3,3,3-trifluoropropyl, or a C₅-C₈ cycloalkyl radical, which is optionally substituted, or an aryl or an aralkyl radical, which is optionally substituted:

in particular with halogens and/or alkoxyls, phenyl, xylyl, tolyl and dichlorophenyl radicals being most particularly selected, and, even more preferably, at least 60 mol % of the radicals R³ being methyls, the symbols Y are similar or different and represent:
either the radical R³, or a cationically crosslinkable organofunctional group, preferably an epoxyfunctional or vinyloxyfunctional group, which is linked to the silicon via a divalent radical containing, advantageously, from 2 to 20 carbon atoms including, optionally, a hetero atom, at least one of the symbols Y corresponding to a cationically crosslinkable organofunctional group.

According to a preferred mode of the invention, the polyorganosiloxane contains from 1 to 10 organofunctional groups per mole. For each epoxyfunctional group, this corresponds to epoxide contents ranging from 20 to 200 molar meq/100 g of product.

As examples of divalent radicals linking an organofunctional group of the epoxy type, there may be mentioned those included in the following formulae (Y):

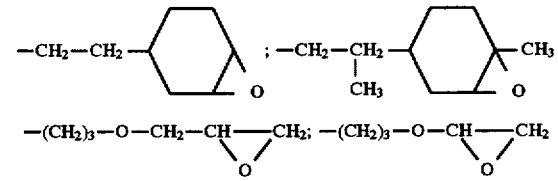

As regards the organofunctional groups of the vinyl ether type, there may be mentioned, e.g., those contained in the following formulae (Y): —(CH₂)₃—O—CH=CH₂; —(CH₃)₂—O—R⁴—O—CH=CH₂
with R⁴= linear or branched C₁-C₁₂ alkylene, which is optionally substituted, or arylene, preferably phenylene, which is optionally substituted, preferably with one to three C₁-C₆ alkyl groups.

The linear polyorganosiloxanes may be oils with a dynamic viscosity at 25° C. of the order of 10 to 10,000 mPa s at 25° C., generally of the order of 50 to 5,000 mPa s at 25° C. and, even more preferably, of 100 to 600 mPa s at 25° C., or gums having a molecular weight of the order of 1,000,000.

The dynamic viscosity at 25° C. of all the silicone polymers considered in the present account may be measured using a Brookfield viscometer, according to AFNOR standard NFT 76 102 of February 1972.

The viscosity being considered in the present account is the dynamic viscosity at 25° C., known as the "Newtonian" viscosity, that is to say the dynamic viscosity which is measured, in a manner known per se, at a shear rate gradient which is low enough for the viscosity measured to be independent of the rate gradient.

Where cyclic polyorganosiloxanes are concerned, these consist of units (IV) which may be, for example, of the dialkylsiloxy or alkylarylsiloxy type. These cycic polyorganosiloxanes have a viscosity of the order of 1 to 5,000 mPa s.

Since this wide variety of polyorganosiloxanes is available, it is entirely conceivable to use a mixture of different products of formulae (IV) and (V), as defined above, within the context of the invention.

The preferred epoxyfunctional or vinyloxyfunctional polyorganosiloxanes are described in particular in the patents: DE-A-4,009,889; EP-A-0,396,130; EP-A-0,355,381; EP-A-0,105,341; FR-A-2,110,115; FR-A-2,526,800.

The epoxyfunctional polyorganosiloxanes may be prepared by hydrosilylation reaction between oils containing Si-H units and epoxyfunctional compounds, such as 4-vinylcyclohexene oxide, allyl glycidyl ether, and the like.

The vinyloxyfunctional polyorganosiloxanes may be prepared by hydrosilylation reaction between oils containing Si-H units and vinyloxyfunctional compounds, such as allyl vinyl ether, allyl-vinyloxyethoxybenzene, and the like.

The polyorganosiloxanes given above by way of example are particularly advantageous, insofar as the accelerators of the benzyl alcohol type, in accordance with the invention, have proved to be fully soluble in these polyorganosiloxanes.

According to the invention, the expression effective catalytic amount of onium borate or of borate of organometallic complexes is understood to mean the amount which is sufficient to initiate the crosslinking. This amount is generally between 0.01 and 20 parts by weight, usually between 0.1 and 8 parts by weight, in order photochemically to crosslink 100 parts by weight of polyorganosiloxanes.

The compositions according to the invention may also comprise at least one photosensitizer selected from (poly) aromatic products (which are optionally metallic) and heterocyclic products, and preferably from the list of the following products: toluene, pyridine, ferrocene, benzene, thioxanthone, anthracene, benzophenone.

Conventionally, the compositions according to the invention may additionally comprise various additives, which are chosen depending on the final application intended. These may be, for example, mineral or non-mineral fillers and/or pigments, such as ground synthetic or natural fibres (polymers), calcium carbonate, talc, clay, titanium dioxide or fumed silica. This may allow e.g. the mechanical characteristics of the final materials to be improved.

The soluble dyes, the oxidation inhibitors, and/or any other material which does not interfere with the catalytic activity of the photoinitiator and which does not absorb within the range of wavelengths chosen for the photoactivation, may also be added to the composition or used within the context of the process according to the invention.

Lastly, the compositions according to the invention may include other ingredients, such as adhesion modifiers (linear silicone polymers or resins bearing vinyl, epoxy, vinyl ether, alcohol functions, and the like), fungicidal, bactericidal and antimicrobial agents, corrosion inhibitors, etc.

It is immaterial whether these compositions in accordance with the invention are prepared before (even a long time before) or immediately before use.

It should be noted that these compositions are particularly stable on storage and that, in accordance with the process of the invention, they offer rapid crosslinking kinetics. In addition, their non-crosslinked state, before exposure to the activating light radiation, offers great ease of handling, of application or of introduction onto the various supports or other shaping moulds.

The compositions according to the invention may be used as they are. They are useful in the field of anti-adhesive coatings on solid supports of any nature, such as cellulosic materials, plastics, metals or ceramics, inter alia on films, paints or for the encapsulation of electrical and electronic components, coatings for textiles, and coatings for the sheathing of optical fibres.

They are most particularly advantageous when they are used without further treatment in order to render a material, such as metal sheets, glass, plastic or paper, non-adhesive with respect to other materials to which it would normally adhere. The composition advantageously has a viscosity not exceeding 5000 mPa s, preferably not exceeding 4000 mPa s, at 25° C.

The invention is also directed towards a process which allows particles (for example sheets) to be rendered non-adhesive with respect to surfaces to which they would normally adhere, which process consists in applying an amount of composition of the invention, generally of between 0.1 and 5 g per $m^2$ of surface to be coated, and in crosslinking the composition by supplying energy, at least some, and preferably all, of which is provided by UV radiation.

The UV radiation used has a wavelength of between 200 and 400 nanometers, preferably of between 254 and 360 nanometers.

The duration of irradiation may be very short and it is generally less than 1 second and is of the order of a few tenths of a second for very thin coatings. The crosslinking achieved is excellent, even in the absence of any heating. Obviously, it is not excluded from the invention to combine the photoactivation with a thermal activation, e.g. by heating to between 25° and 100° C.

Obviously, it is possible to adjust the curing time, in particular by the number of UV lamps used, by the duration of exposure to the UV and by the distance between the composition and the UV lamp.

The amounts of compositions deposited on the supports are variable and usually range between 0.1 and 5 $g/m^2$ of surface treated. These amounts depend on the nature of the supports and on the desired anti-adhesive properties. They are more usually between 0.5 and 3 $g/m^2$ for non-porous supports.

The subject of the present invention is also the articles (for example sheets) consisting of a solid material (metal, glass, plastic, paper, and the like) which is at least partly coated with the composition described above, this composition being at least partially crosslinked.

The examples which follow are given by way of illustration and cannot be considered as limiting the field and spirit of the invention.

BRIEF DESCRIPTION OF THE DRAWING

The figure represents the changes in output voltage of the VNC in mV as a function of time.

EXAMPLES

Examples 1 to 6

I—Starting materials

I.1. The functionalized polyorganosiloxanes used are (1,2-epoxy-4-ethylcyclohexyl) -polydimethylsiloxanes of formula:

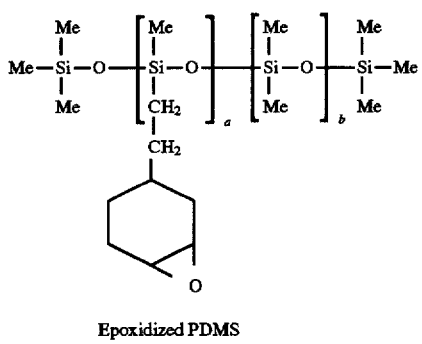

Epoxidized PDMS a and b, and hence the epoxy content, vary according to Examples 1 to 7:

Comparative Example 1 and Examples 2 to 4:
a=4.5, b=115

Comparative Example 5 and Examples 6 to 8:

| EXAMPLE | a | b |
|---------|-----|-----|
| 5 | 8 | 110 |
| 6 | 5.3 | 109 |
| 7 | 8 | 110 |
| 8 | 6 | 48 |

L2. The initiator is an onium borate: ditolyliodonium tetrakis (pentafluorophenyl) borate of formula:

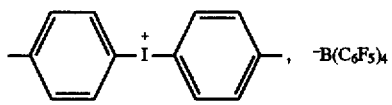

The cation of this onium borate is prepared according to the general methodology described in European Patent Applications Nos. 0,562,922 and 0,562,897. As regards the anionic borate species, the procedure is as follows:

Bromopentafluorobenzene (21.3 g, 0.086 mol) and isopropyl ether are loaded, under an inert atmosphere, into a 500 ml round-bottomed flask fitted with a mechanical stirrer, a condenser and a dropping funnel. The mixture is stirred and is cooled to a temperature of −78° C. using an acetone+cardice bath.

n-Butyllithium in solution in hexane (1.6 M, 52.3 ml, 0.97 eq) is loaded into the dropping funnel and is then added over about 10 minutes. The mixture is then left stirring for 30 minutes at the temperature of −78° C. The dropping funnel is replaced by a dropping funnel containing boron trichloride in solution in hexane (1.0 M, 19 ml). The boron trichloride is added over 15 min, and the reaction mixture is then left stirring for 30 min. at the temperature of −78° C. The mixture is then allowed to warm to room temperature over about 1 h. Saturated aqueous KCl solution (100 ml) is then added. This gives a two-phase, homogeneous mixture. The isopropyl ether is distilled off. The abovementioned $KB(C_6F_5)_4$ precipitates out at the end of the distillation. It is recovered by filtration and is then washed with saturated KCl solution (100 ml), before before being dried under vacuum at a temperature of 35° C.

A product assaying at 97% of expected product is thus obtained, in a yield of 99%.

the accelerators used according to the invention are the benzyl alcohols of the following formulae:

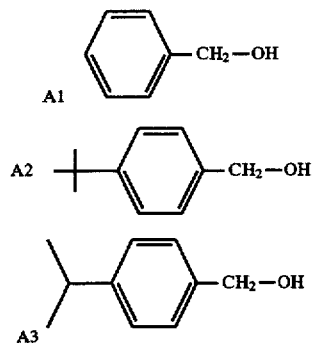

The photoinitiator system is prepared by dissolving the onium borate (with some of the epoxidized PDMS to be used being optionally added), in isopropyl alcohol (IPA) for Comparative Examples 1 and 5, and in accelerator A1 (Example 2), A2 (Example 3) or A3 (Examples 4 and 6 to 8).

II. The general procedure followed is as follows:

to 100 parts by weight of epoxidized PDMS is added 0.9 part by weight of a solution of onium borate (initiator 0.3 part by weight) in isopropyl alcohol (Comparative Examples 1 and 5) or in accelerators A1, A2 and A3 (Examples 2, 3, 4 and 6 to 8 respectively) (0.6 part by weight), and the mixture is stirred manually for 30 min.

III. Tests

III.1 Reactivity tests (Examples 1 to 4)

The reactivity tests described in the following examples were carried out on a VNC (vibrating needle curometer) freezing point measuring machine, marketed by the company RAPRA Ltd., to which a UV-irradiating device was added. During the crosslinking, the VNC needle inserted into the test mixture encounters a resistance which is manifested by a decrease in the output voltage of the machine. The time required to achieve a 10, 50 and 90% decrease in the voltage, for a thickness to be polymerized of 2 mm, is measured.

III.2 Evaluation of the delamination forces by peeling tests

This evaluation is performed, after the formulation of the silicone coating, in the following steps:

coating of the mixture onto a PET 6028 polyester film (marketed by RHONE-POULENC) using a Meyer bar. The thickness deposited may range from 1 to 4 μm (deposition rate ranging from 0.5 to 3 $g/m^2$), crosslinking of the coating under UV at a wavelength of 360 nm with an irradiation power of 120 $W/cm^2$, bonding of three representative types of adhesive to the crosslinked coating:

TESA® 4154 (rubber)
TESA® 4651 (rubber)
TESA® 4970 (acrylic)

placing under a press (70 $g/m^2$) for 20 to 24 hours:

under cold conditions (22°–23° C.) for adhesives 4154 and 4970, FINAT test No. 10 under hot conditions (70° C.) for adhesive 4651, FINAT test No. 11.

* The level of adhesion may then be evaluated by measuring the force of delamination or peeling.

This force is measured by a dynamometer which peels the adhesives off at a speed of 300 mm/min. The result is given in g/cm.

IV. Results

IV.1 Reactivity Examples 1 to 4

The results are given by the curves in the single figure attached. These curves represent the change in output voltage of the VNC in mV as a function of time. Table 1 below gives the times, in min., necessary to achieve a 10, 50 and 90% decrease in the voltage.

TABLE 1

| VOLTAGE DECREASE | 10% | 50% | 90% |
|---|---|---|---|
| Example 1 | 1.75 | 2.15 | 2.45 |
| Example 2 | 1.40 | 1.75 | 2.20 |
| Example 3 | 1.30 | 1.70 | 2.00 |
| Example 4 | 1.30 | 1.55 | 1.90 |

IV. Peeling forces Examples 5 to 8

Table 2 below gives the anti-adhesion results obtained for three adhesives.

TABLE 2

| | EPOXY CONTENT IN molar meq/ | ANTI-ADHESION (g/cm) Adhesives | | |
|---|---|---|---|---|
| EXAMPLE | 100 g PDMS | 4154 | 4970 | 4651 |
| 5 | 94 | 2.05 | 15.4 | 65.00 |
| 6 | 63 | 0.99 | 5.48 | 4.66 |
| 7 | 94 | 1.72 | 10.41 | 20.07 |
| 8 | 126 | 10.94 | 23.85 | 64.51 |

Examples 9 To 12: Coating Tests

I. Starting materials and experimental conditions silicone oil=epoxidized PDMS in which a=8 and b=110, photoinitiator=

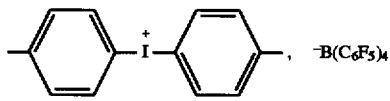, $B(C_6F_5)_4^-$ coating on glassine® 9564 paper (marketed by the company Sibille). This coating is carried out as described in Examples 5 to 8 above, adhesives: these are the same as for Examples 1 to 8 (cf. III.2 above), lamp power=120W (FUSION TYPE H).

II—Results

After passing under the UV lamp, the throughput in m/min necessary for curing is noted.

The extractable percentage corresponding to the non-crosslinked PDMS, which is present in the cured coating layer and which is extractable by solvents, is measured in a manner known per se.

The weight analysis of the extractable PDMS is carried out by IR spectrometry.

The anti-adhesion measuring procedure is the same as for Examples 5 to 8.

Table 3 below gives test conditions and the results obtained.

TABLE 3

| EXAMPLE No. | Accelerator | Speed (m/min) | % extractables | ANTI-ADHESION g/cm adhesives | | |
|---|---|---|---|---|---|---|
| | | | | 4154 | 4970 | 4651 |
| 9 | IPA | 150 | 7.4 | 3.0 | 10.0 | 24.0 |
| 10 | $A_3$ | 150 | 6.7 | 2.8 | 8.2 | 21.0 |
| 11 | IPA | 200 | 14.5 | 2.0 | 10.0 | 26.0 |
| 12 | $A_3$ | 200 | 11.7 | 1.0 | 8.3 | 22.5 |

Examples 9 and 11 are comparative to Examples 10 and 12.

III—Comments

Lower adhesion forces are found systematically, for the same speed, when $A_3$ according to the invention is used, thereby reflecting a more complete polymerization. Furthermore, the extractable percentages are lower with $A_3$ according to the invention, thereby confirming the better crosslinking obtained when compared with the IPA controls.

I claim:

1. An initiator for the cationic polymerization and/or crosslinking, under photochemical and/or thermal activation and/or activation by a beam of electrons, of monomers and/or polymers containing organofunctional groups, said initiator comprising an effective catalytic amount of at least one onium salt of an element from groups 15 to 17 of the Periodic Table and/or of at least one organometallic complex of an element from groups 4 to 10 of the Periodic Table, comprising at least one polymerization or crosslinking accelerator chosen from proton-donating organic solvents of aromatic nature.

2. The initiator as claimed in claim 1, in which the accelerator is formed of at least one benzyl alcohol of the following general formula (I):

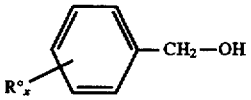  (I)

in which:

R° is an electron-donating or electron-accepting group, preferably an electron-accepting group, chosen from linear or branched $C_1$–$C_{12}$ (cyclo)alkyls and (cyclo)alkoxyls, aryls, which are optionally substituted preferably with halogens, or radicals of the type $NO_2$ etc., x is an integer from 0 to 5, and the groups R° being identical to or different from each other when x>1, the formulae (I) in which x=0 or those in which x>0 with R° representing a methyl, t-butyl or isopropyl group, being particularly preferred.

3. The initiator as claimed in claim 1 or claim 2, which: comprises an effective catalytic amount of an onium borate, the cationic species of which is chosen from:

1) the onium salts of formula (II)

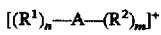  (II)

in which formula:

A represents an element from groups 15 to 17, such as I, S, Se, P, N, etc., $R^1$ represents a $C_6$–$C_{20}$ carbocyclic or heterocyclic aryl radical, preferably phenyl, tolyl or toluyl, it being possible for said heterocyclic radical to contain nitrogen or sulfur as hetero elements, $R^2$ represents $R^1$ or a $C_1$–$C_{30}$ linear or branched alkyl or alkenyl radical, said radicals $R^1$ and $R^2$ being optionally substituted with a $C_1$–$C_{25}$ alkoxy, $C_1$–$C_{25}$ alkyl, nitro, chloro, bromo, cyano, carboxyl, mercapto, etc. group, n is an integer ranging from 1 to v+1, v being the valency of the element A, m is an integer ranging from 0 to v–1 with n+m =v+1, 2) the oxoisothiochromanium salts, in particular the sulfonium salt of 2-ethyl-4-oxoisothiochromanium or of 2-dodecyl-4-oxoisothiochromanium, 3) the organometallic salt of formula (II bis):

$$(L^1 L^2 L^3 M)^{+q}$$

in which formula:

M is a metal from Groups 4 to 10 of the Periodic Table; $L^1$ is one ligand joined to the metal M via π electrons, said ligand being selected from among the η³-alkyl, η⁵-cyclopentadienyl and η⁷-cycloheptatrienyl ligands and the η⁶-aromatic compounds selected from among the optionally substituted η⁶-benzene ligands and the compounds having from 2 to 4 condensed rings, each ring being capable of contributing to the valence shell of the metal M via 3 to 8 π electrons; $L^2$ is one ligand joined to the metal M via π electrons, said ligand being selected from among the η⁷-cycloheptatrienyl ligands and the η⁶-aromatic compounds selected from among the optionally substituted η⁶-benzene ligands and the compounds having from 2 to 4 condensed rings, each ring being capable of contributing to the valence shell of the metal M via 6 or 7 π electrons; $L^3$ is from 0 to 3 identical or different ligands joined to the metal M via σ electrons, said ligand(s) being selected from among CO and $NO_2^+$, with the proviso that the total electron charge q of the complex to which $L^1$, $L^2$ and $L^3$ contribute and the ionic charge of the metal M are positive and equal to 1 or 2, the anionic borate species of which has the formula (III):

$$[BX_aR_b]$$  (III)

in which formula:

a and b are integers ranging from 0 to 4 with a+b=4, the symbols X represent:
   a halogen atom with a=0 to 3; or
   an OH function with a=0 to 2, the symbols R are identical or different and represent:
   a phenyl radical substituted with at least one electron-attracting group such as $CF_3$, $NO_2$, CN, etc., or with at least two halogen atoms;
   an aryl radical containing at least two aromatic rings which is optionally substituted with at least one electron-attracting element or group.

4. The initiator as claimed in claim 3, in which the anionic borate species is:

[B(C₆F₅)₄]⁻ [B(C₆H₄CF₃)₄]⁻ [B(C₆H₃(CF₃)₂)₄]⁻

[(C₆F₅)₂BF₂]⁻ [C₆F₅BF₃]⁻ [B(C₆H₃F₂)₄]⁻

5. The initiator as claimed in claim 3, in which the cationic species is of the onium type and is preferably chosen from the following species:

[(Φ)₂I]⁺ [C₈H₁₇—O-Φ-I-Φ]⁺ [(Φ-CH₃)₂I]⁺

-continued

[C₁₂H₂₅-Φ-I-Φ]⁺ [(C₈H₁₇—O-Φ)₂I]⁺ [(Φ)₃S]⁺

[(Φ)₂-S-Φ-O—C₈H₁₇]⁺ [Φ-S-Φ-S-(Φ)₂]⁺

[(C₁₂H₂₅-Φ)₂I]⁺

6. The initiator as claimed in claim 3, in which the onium borate is:

[(Φ-CH₃)₂I]⁺[B(C₆F₅)₄]⁻ [(Φ)₂I]⁺[B(C₆F₅)₄]⁻

[Φ₂I]⁺[B(C₆H₃(CF₃)₂)₄]⁻ [C₁₂H₂₅-Φ-I-Φ]⁺[B(C₆F₅)₄]⁻

[(C₈H₁₇—O-Φ)₂I]⁺[B(C₆F₅)₄]⁻

[(C₈H₁₇)—O-Φ-I-Φ]⁺[B(C₆F₅)₄]⁻ [(Φ)₃S]⁺[B(C₆F₅)₄]⁻

[(Φ)₂S-Φ-O—C₈H₁₇]⁺[B(C₆H₄CF₃)₄]⁻

[(C₁₂H₂₅-Φ)₂I]⁺[B(C₆F₅)₄]⁻

7. A composition based on at least one cationically crosslinkable polyorganosiloxane and on at least one initiator as claimed in claim 1.

8. The composition as claimed in claim 7, in which the polyorganosiloxane has organofunctional groups of the epoxide and/or vinyl ether type and in which it is chosen from the polyorganosiloxanes which are:

either linear or substantially linear and consist of units of formula (IV), ending with units of formula (V), or cyclic and consist of units of formula (IV):

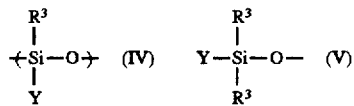

in which formulae:
the symbols $R^3$ are similar or different and represent:
   either a linear or branched $C_1$–$C_6$ alkyl radical, which is optionally substituted, advantageously with one or more halogens, the optionally substituted alkyl radicals preferred being: methyl, ethyl, propyl, octyl and 3,3,3-trifluoropropyl,
   or a $C_5$–$C_8$ cycloalkyl radical, which is optionally substituted,
   or an aryl or an aralkyl radical, which is optionally substituted:
      in particular with halogens and/or alkoxyls,
      phenyl, xylyl, tolyl and dichlorophenyl radicals being most particularly selected,
   and, even more preferably, at least 60 mol % of the radicals $R^3$ being methyls, the symbols Y are similar or different and represent:
   either the radical $R^3$,
   or a cationically crosslinkable organofunctional group, preferably an epoxyfunctional or vinyloxyfunctional group, which is linked to the silicon via a divalent radical containing, advantageously, from 2 to 20 carbon atoms including, optionally, a hetero atom, at least one of the symbols Y corresponding to a cationically crosslinkable organofunctional group.

9. The composition as claimed in claim 8, in which the polyorganosiloxane contains from 1 to 10 organofunctional groups per mole.

10. The composition as claimed in claim 8, in which said polyorganosiloxane is linear and has a viscosity at 25° C. of the order of 10 to 10,000 mPa s.

11. A process for rendering articles non-adhesive with respect to surfaces to which they would normally adhere, in which between 0.1 and 5 g of composition forming the subject of claim 7 is applied per m² of surface of said article to be coated, and in which said composition is crosslinked photochemically and/or thermally and/or by a beam of electrons.

12. The process as claimed in claim 11, in which the crosslinking operation is performed by photoactivation using UV radiation with a wavelength of the order of 200 to 400 nanometers, said photoactivation optionally being combined with a thermal activation.

13. An article which is at least partly coated with at least one film comprising a composition as claimed in claim 7 which composition is at least partially crosslinked.

* * * * *